United States Patent
Barak

(10) Patent No.: US 10,576,045 B2
(45) Date of Patent: Mar. 3, 2020

(54) LOW DOSAGE COMBINATIONS OF FLUOXETINE AND REBOXETINE FOR TREATING OBESITY

(76) Inventor: Nir Barak, Tel Aviv (IL)

( * ) Notice: Subject to any disclaimer, the term of this patent is extended or adjusted under 35 U.S.C. 154(b) by 563 days.

(21) Appl. No.: 14/378,418

(22) PCT Filed: Feb. 15, 2012

(86) PCT No.: PCT/IL2012/050049
§ 371 (c)(1),
(2), (4) Date: Aug. 13, 2014

(87) PCT Pub. No.: WO2012/111011
PCT Pub. Date: Aug. 23, 2012

(65) Prior Publication Data
US 2015/0335649 A1    Nov. 26, 2015

(51) Int. Cl.
| | |
|---|---|
| *A61K 31/135* | (2006.01) |
| *A61K 31/535* | (2006.01) |
| *A61K 31/138* | (2006.01) |
| *A61K 31/5375* | (2006.01) |
| *A61K 45/06* | (2006.01) |
| *A61K 31/343* | (2006.01) |
| *A61K 31/4188* | (2006.01) |
| *A61K 31/137* | (2006.01) |
| *A61K 31/4525* | (2006.01) |
| *A61K 31/496* | (2006.01) |

(52) U.S. Cl.
CPC .......... *A61K 31/138* (2013.01); *A61K 31/135* (2013.01); *A61K 31/137* (2013.01); *A61K 31/343* (2013.01); *A61K 31/4188* (2013.01); *A61K 31/4525* (2013.01); *A61K 31/496* (2013.01); *A61K 31/5375* (2013.01); *A61K 45/06* (2013.01)

(58) Field of Classification Search
CPC ...................... A61K 31/135; A61K 31/5355
USPC .............................................. 514/651, 239.2
See application file for complete search history.

(56) References Cited

U.S. PATENT DOCUMENTS

| | | | |
|---|---|---|---|
| 6,964,962 B2 | 11/2005 | Wong et al. | |
| 7,375,111 B2 * | 5/2008 | Weber ................. | A61K 31/135 514/282 |
| 7,528,108 B2 * | 5/2009 | Tsai ..................... | A61K 31/315 424/9.1 |
| 7,754,748 B2 | 7/2010 | Gadde et al. | |
| 2005/0009927 A1 | 1/2005 | Marek et al. | |
| 2005/0014848 A1 | 1/2005 | Marek et al. | |
| 2005/0059715 A1 | 3/2005 | Dooley et al. | |
| 2005/0143350 A1 | 6/2005 | Seed | |
| 2006/0148787 A1 | 7/2006 | Barak | |
| 2007/0275970 A1 | 11/2007 | Weber et al. | |
| 2008/0113026 A1 | 5/2008 | McKinney et al. | |
| 2010/0040680 A1 | 2/2010 | Lai et al. | |

FOREIGN PATENT DOCUMENTS

| | | | |
|---|---|---|---|
| EP | 1870096 | 12/2007 | |
| EP | 2260844 A1 * | 12/2010 | ........... A61K 31/343 |
| WO | 2009/035473 | 3/2009 | |

OTHER PUBLICATIONS

Simon et al., Arch Gen Psychiatry. 2006;63(7):824-830.*
Fleishaker, et al., Clin Drug Invest Aug. 1999; 18 (2): 141-150.*
Goldstein et al., "Fluoxetine: a randomized clinical trial in the treatment of obesity", International Journal of Obesity, vol. 18(3), (1994): 129-135.
Hudson et al., "Binge-eating disorder as a distinct familial phenotype in obese individuals", Arch Gen Psychiatry, vol. 63(3), Mar. 2006: 313-319.
Jimerson et al., "Low serotonin and dopamine metabolite concentrations in cerebrospinal fluid from bulimic patients with frequent binge episodes", Arch Gen Psychiatry, vol. 49(2), Feb. 1992: 132-138.
Poyurovsky et al., "Attenuation of olanzapine-induced weight gain with reboxetine in patients with schizophrenia: a double-blind, placebo-controlled study", Am J Psychiatry, vol. 160(2), Feb. 2003: 297-302.
Poyurovsky et al., "Attenuating effect of reboxetine on appetite and weight gain in olanzapine-treated schizophrenia patients: a double-blind placebo-controlled study", Psychopharmacology, vol. 192(3), (2007): 441-448.
Silveira et al., "An open trial of reboxetine in obese patients with binge eating disorder", Eat Weight Disord., vol. 10(4), Dec. 2005: e93-e96.
Snitker et al., "The sympathetic nervous system and obesity: role in aetiology and treatment", Obesity Reviews 1(1), (2000): pp. 5-15.

(Continued)

*Primary Examiner* — Shengjun Wang
(74) *Attorney, Agent, or Firm* — Dorsey & Whitney LLP

(57) ABSTRACT

The present invention provides a pharmaceutical composition comprising a selective serotonin reuptake inhibitor (SSRI) and a norepinephrine reuptake inhibitor (NRI), particularly, fluoxetine and reboxetine, for treating obesity. Surprisingly, the inventor of the present invention discovered that use of especially low doses of the active compounds, particularly, at most 6 mg/day of reboxetine and at most 20 mg/day of fluoxetine, wherein the reboxetinerfluoxetine ratio is from about 1:4 to about 1:6, induces an effective weight loss in obese patients. Advantageously, the combinations of the present invention include very low doses of the active ingredients, thereby decreasing possible drug-drug interactions and adverse drug reaction.

7 Claims, No Drawings

(56) References Cited

OTHER PUBLICATIONS

Weiss et al., "Inhibition of P-glycoprotein by newer antidepressants", The Journal of Pharmacology and Experimental Therapeutics, vol. 305(1), (2003): pp. 197-204.
Fleishaker (2000) Clinical pharmacokinetics of reboxetine, a selective norepinephrine reuptake inhibitor for the treatment of patients with depression. Clin Pharmacokinet 39(6): 413-27.
Goldstein et al., (1993) Fluoxetine: a randomized clinical trial in the maintenance of weight loss. Obes Res 1(2): 92-98.
Penttilä et al., (2004) Effects of fluoxetine on dopamine D2 receptors in the human brain: a positron emission tomography study with [11C]raclopride. Int J Neuropsychopharmacol 7(4): 431-439.
Levine et al., (1989) Use of fluoxetine, a selective serotonin-uptake inhibitor, in the treatment of obesity: a dose-response study (with a commentary by Michael Weintraub). Int J Obes 13(5): 635-645.

\* cited by examiner

LOW DOSAGE COMBINATIONS OF FLUOXETINE AND REBOXETINE FOR TREATING OBESITY

FIELD OF THE INVENTION

The present invention relates to a pharmaceutical composition for improved treatment of obesity. In particular, the present invention relates to compositions comprising a combination of norepinephrine reuptake inhibitors and selective serotonin reuptake inhibitors, and use thereof for treating obesity including reducing the severity of obesity.

BACKGROUND OF THE INVENTION

Obesity and overweight have become a major health threat in humans with an immense impact to public health. Obesity and overweight pose a major risk for serious chronic diseases, including type II diabetes, cardiovascular disease, dyslipidemia, sleep apnea, hypertension and stroke, and certain forms of cancer. The risk of comorbidities of obesity, including mortality, increase with increasing body mass index (BMI). Obesity is also associated with serious social and psychological aspects, affecting virtually all ages and socioeconomic groups.

According to certain publications, obesity may be divided into two types, obesity with binge eating disorder (BED) and obesity without BED, since BED appears to represent a distinct familial phenotype in obese individuals (e.g. Hudson et al. Arch Gen Psychiatry. 2006, 63(3):313-9).

Drugs prescribed for obesity may reduce fat absorption or regulate satiety via their action on serotonergic, norepinephric, dopaminergic or the cannabinoid receptor systems in the brain (e.g. Jimerson et al., Arch. Gen. Psychiatry, 49:132-138, 1992). The effects of the sympathetic nervous system (SNS) on metabolism were shown to be associated with development and maintenance of obesity, and accordingly, the SNS has been suggested as a potential therapeutic target in the treatment of obesity (e.g. Snitker et al. Obes Rev. 2000,1(1):5-15).

Reboxetine is a norepinephric reuptake inhibitor (NRI) used in the treatment of acute depression, panic disorder and attention-deficit/hyperactivity disorder (ADHD). Obese patients with BED treated with 8 mg/day of reboxetine for 12 days, showed reduced binge eating behavior (Silverio et al. Eat Weight Disord. 2005, 10(4):e93-6). It has also been disclosed that coadministering reboxetine (4 mg/day) with the atypical antipsychotic olanzapine, reduced the weight-gain associated with olanzapine administration (Poyurovski. Psychopharmacology (Berl), 2007, 192(3):441-8).

Fluoxetine is a selective serotonin reuptake inhibitor (SSRI) mostly prescribed as an anti-depressant and also used for the treatment of obsessive compulsive disorder and bulimia nervosa. Fluoxetine, administered at a dose of 60 mg/day, showed statistically significant weight loss compared to placebo following 28 weeks of treatment. However, at the end of the study (at week 52) no difference between treatment and placebo groups was observed (Goldstein et al. Int J Obes Relat Metab Disord. 1994, 18(3):129-35).

Combinations of SSRIs and NRIs for treating indications other than eating disorders are known. For example, U.S. Patent Application No. 2005/0059715 discloses a combination therapy for the treatment of pain comprising a synergistic amount of an alpha-2-delta ligand and a dual serotonin norepinephrine reuptake inhibitor or one or both of an SSRI and an NRI, or pharmaceutically acceptable salts thereof.

A combination of SSRIs, including fluoxetine, and NRIs, including reboxetine, for treating and preventing an extensive list of disorders, eating disorders among others, is disclosed in U.S. Patent Application, Publication No. 2005/0014848. It is further discloses that the SSRI and the NRI may be administered in one or more unit doses each comprising 1 to 300 mg of the active component, but does not specify any preferred amounts or ratios between said components.

U.S. Patent Application, Publication No. 2007/0275970, discloses a method for affecting weight loss, comprising administering an opioid antagonist together with a second compound, such as, a combination of an SSRI and an NRI.

PCT Publication No. WO 2009/035473 discloses a method of treating binge eating disorder or obesity resulting from binge eating behavior, comprising providing an effective amount of amphetamine prodrug, methylphenidate prodrug, or methylphenidate analog to a patient, as the only active agent or together with one or more additional active agents, including antidepressants such as SSRIs and NRIs.

There is a recognized medical need for an effective and specific treatment of obesity.

SUMMARY OF THE INVENTION

The present invention provides a pharmaceutical composition comprising a selective serotonin reuptake inhibitor (SSRI) and a norepinephrine reuptake inhibitor (NRI), particularly, fluoxetine and reboxetine, for treating obesity. Surprisingly, the inventor of the present invention discovered that use of especially low doses of the active compounds, particularly, at most 6 mg/day of reboxetine and at most 20 mg/day of fluoxetine, wherein the reboxetine:fluoxetine ratio is from about 1:4 to about 1:6, induces an effective weight loss in obese patients. Advantageously, the combinations of the present invention include very low doses of the active ingredients, thereby decreasing possible drug-drug interactions and adverse drug reaction.

According to one aspect, the present invention provides a pharmaceutical composition comprising at least one NRI and at least one SSRI, wherein the amount of the at least one NRI is at most 6 mg and the amount of the at least one SSRI is at most 20 mg and wherein the NRI:SSRI ratio is within the range of 1:4 to 1:6.

According to one embodiment, the at least one NRI is selected from the group consisting of: atomoxetine, viloxazine, mazindol and reboxetine. According to another embodiment the at least one NRI is reboxetine.

According to yet another embodiment, the at least one SSRI is selected from the group consisting of: sertaline, dapoxetine, vilazodone, citalopram, escitalopram, paroxetine, fluvoxamine and fluoxetine. According to yet another embodiment, the at least one SSRI is fluoxetine.

According to yet another embodiment the amount of the at least one NRI is within the range of 0.1 mg to 6 mg.

According to yet another embodiment the amount of the at least one SSRI is within the range of 0.1 mg to 20 mg.

According to yet another embodiment the NRI:SSRI ratio is 1:5

According to another aspect, the present invention provides a pharmaceutical composition comprising reboxetine and fluoxetine, wherein the amount of reboxetine is at most 6 mg and the amount of fluoxetine is at most 20 mg and wherein the ratio of reboxetine to fluoxetine is within the range of 1:4 to 1:6. According to one embodiment the ratio of reboxetine to fluoxetine is about 1:5

According to another embodiment, the amount of reboxetine is within the range of 0.1 mg to 6 mg. According to yet another embodiment the amount of fluoxetine is within the range of 0.1 mg to 20 mg.

According to yet another aspect, the present invention provides a method for treating obesity, comprising administering to a subject in need thereof a pharmaceutical composition comprising at least one NM and at least one SSRI, wherein the amount of the at least one NRI is at most 6 mg/day and the amount of the at least one SSRI is at most 20 mg/day and wherein the NRI:SSRI ratio is within the range of 1:4 to 1:6.

According to yet another aspect, the present invention provides a method for treating obesity, comprising administering to a subject in need thereof a pharmaceutical composition comprising reboxetine and fluoxetine, wherein the amount of reboxetine is at most 6 mg/day and the amount of fluoxetine is at most 20 mg/day and wherein the reboxetine:fluoxetine ratio is within the range of 1:4 to 1:6.

According to yet another aspect, the present invention provides a pharmaceutical composition for the treatment of obesity, comprising at least one NRI and at least one SSRI, wherein the amount of the at least one NRI is at most 6 mg/day and the amount of the at least one SSRI is at most 20 mg/day and wherein the NRI:SSRI ratio is within the range of 1:4 to 1:6.

According to yet another aspect, the present invention provides a pharmaceutical composition for the treatment of obesity, comprising reboxetine and fluoxetine, wherein the amount of reboxetine is at most 6 mg/day and the amount of fluoxetine is at most 6 mg20 mg/day and wherein the reboxetine:fluoxetine ratio is within the range of 1:4 to 1:6.

According to some embodiments, the pharmaceutical composition of the invention further comprises pharmaceutically acceptable excipients, carriers, and diluents. According to other embodiments, the pharmaceutical composition is in the form of tablets, chewable tablets, capsules, syrups, suspensions, solutions, intranasal sprays, suppositories, transdermal patches, among other types of pharmaceutical compositions. Each possibility is a separate embodiment of the invention.

According to other embodiments, the pharmaceutical composition is a long acting, controlled release, extended release or slow release formulation. Each possibility is a separate embodiment of the invention.

According to other embodiments, the pharmaceutical composition is administered to the subject by a route selected from oral, transdermal, percutaneous, intravenous, intramuscular, intranasal and intrarectal. Each possibility is a separate embodiment of the invention.

According to yet another aspect, the present invention provides a method for treating obesity comprising administering to a subject in need thereof a combined therapy comprising at least one NRI and at least one SSRI, wherein the amount of the at least one NRI is at most 6 mg/day and the amount of the at least one SSRI is at most 20 mg/day and wherein the NRI:SSRI ratio is within the range of 1:4 to 1:6.

According to yet another aspect, the present invention provides a method for treating obesity comprising administering to a subject in need thereof a combined therapy comprising reboxetine and fluoxetine, wherein the amount of reboxetine is at most 6 mg/day and the amount of fluoxetine is at most 20 mg/day and wherein the reboxetine:fluoxetine ratio is within the range of 1:4 to 1:6.

According to one embodiment, the active ingredients are administered in fixed intervals, at variable intervals, sequentially or concurrently. Each possibility is a separate embodiment of the invention.

According to yet another embodiment the daily dose of the at least one NRI and the at least one SSRI is administered in a single dose once a day or in smaller doses at least twice daily at fixed or variable intervals. Each possibility is a separate embodiment of the invention.

According to some embodiments, obesity is selected from the group consisting of: overweight and binge eating disorder.

According to yet another aspect, the present invention provides a kit for treating obesity in a subject of need thereof comprising:

(a) at least one NRI and a pharmaceutically acceptable carrier or diluents in a first unit dosage form, wherein the amount of the at least one NRI is at most 6 mg;

(b) at least one SSRI and a pharmaceutically acceptable carrier or diluents in a second unit dosage form, wherein the amount of the at least one SSRI is at most 20 mg; and (c) container means to contain the first and second dosage forms, wherein the ratio of the first unit dosage form to the second unit dosage form is in the range of 1:4 to 1:6.

According to one embodiment the at least one NRI is reboxetine. According to another embodiment the at least one SSRI is fluoxetine. According to yet another embodiment the ratio of the first unit dosage form to the second unit dosage form is about 1:5.

According to yet another embodiment the first and second unit dosage forms are contained in a single container. According to yet another embodiment the first unit dosage form and the second unit dosage form are contained in separate containers.

Further embodiments, features, advantages and the full scope of applicability of the present invention will become apparent from the detailed description given hereinafter. However, it should be understood that the detailed description, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention discloses the use of a combination of a selective serotonin reuptake inhibitor and a norepinephrine reuptake inhibitor for the treatment of obesity. A method for weight loss in obese patients is further disclosed.

The present invention relies upon the unexpected finding that administration of reboxetine at a dose of at most 6 mg/day and fluoxetine at a dose of at most 20 mg/day, provided at a ratio of about 1:5, induces weight loss. Particularly, subjects administered with 2 mg/day of reboxetine and 10 mg/day of fluoxetine, reduced about 1 kg/week of their initial weight.

The term "about 1:5" as used herein, refers to any numerical value representing a ratio within the range of 1:4 to 1:6.

According to the World Health Organization (WHO) obesity has reached epidemic proportions globally, with more than one billion adults overweight, with at least 300 million of them diagnosed as clinically obese.

The term "overweight" as used herein, refers to a body mass index (BMI) of 25 to 29.9 kg/m². The term "obesity" as used herein refers to a BMI of ≥30 kg/m².

Obesity results when energy intake exceeds expenditure, thus the excess calories are stored in adipose tissue. Obesity is a well-known risk factor for the development of various diseases such as hypertension, heart diseases, dyslipidemia, sleep apnea, diabetes and certain types of cancer. The high and increasing prevalence of obesity throughout the world thereby impacts directly on the incidence of the aforementioned diseases. It has been shown that individuals with mild obesity, defined as a BMI between 30 and 35, have also an increased risk of comorbidities.

It is known that appetite is mainly controlled by discrete areas in the hypothalamus: a feeding centre in the ventrolateral nucleus of the hypothalamus (VLH) and a satiety centre in the ventromedial hypothalamus (VMH). The cerebral cortex receives positive signals from the feeding centre that stimulate eating, and the satiety centre modulates this process by sending inhibitory impulses to the feeding centre. The hypothalamic centers are sensitive to catecholamine signals which further modulate eating behavior. Additionally, it is well established that the serotonin (5-hydroxytryptamine) system plays critical roles in the regulation of energy homeostasis and in the processes of meal satiation and satiety.

It is to be understood that employing the compositions of the present invention for the treatment of overweight individuals that do not fall under the definition of obesity is also encompassed within the scope of the present invention. The compositions of the present invention may be used for medical weight loss as well as for non-medical weight loss.

The terms "binge eating disorder", "BED", and "binge eating behavior" are interchangeably used herein for describing a form of eating disorder defined by the DSM-IV as Eating Disorder Not Otherwise Specified. Binge eating disorder is characterized by recurrent binge eating episodes, which include eating larger amounts of food than normal during a short period of time and a lack of control over eating during the binge episode.

The terms "norepinephrine reuptake inhibitors" and "NRIs" are interchangeably used herein to describe a class of medication commonly used for a wide variety of clinical indications including mood disorders, depression, ADHD and hypotension amongst others. NRIs mode of action is primarily by blocking the norepinephrine transporter thereby obtaining higher levels of norepinephrine and epinephrine in the neuronal synapse, which leads to an increase in norepinephric transmission.

The terms "selective serotonin reuptake inhibitors", "serotonin reuptake inhibitors" and "SSRIs" are interchangeably used herein to describe a class of medication used primarily to treat psychiatric disorders, including depression, obsessive-compulsive disorder and others. The SSRIs are believed to exert their therapeutic action by blocking neuronal uptake of serotonin (5-hydroxytryptamine), thereby resulting in increased levels of serotonin. The use of SSRI has also been shown to be effective in metabolic disorders that are affected by serotonin levels.

The present invention provides a pharmaceutical composition comprising at least one NRI and at least one SSRI, wherein the amount of the NRI is at most 6 mg and the amount of the SSRI is at most 20 mg and wherein the ratio of the NRI to SSRI is within the range of 1:4 to 1:6. According to a preferred embodiment the ratio of the NRI to SSRI is 1:5.

The amount of the NRI may be within the range of 0.1 mg to 6 mg and the amount of the SSRI may be within the range of 0.1 mg to 20 mg.

The NRI may be selected from the group consisting of: atomoxetine, viloxazine, mazindol and reboxetine. The SSRI may be selected from the group consisting of: sertaline, dapoxetine, vilazodone, citalopram, escitalopram, paroxetine, fluvoxamine and fluoxetine. It is to be understood that these lists are meant to give examples of representative NRIs and SSRIs and are not restrictive in the context of the present invention.

It will be understood that while the use of a single NM and a single SSRI are preferred, combinations of two or more NRIs and two or more SSRIs are acceptable if desired, provided the overall ratio of the NRIs to SSRIs remains in the range of 1:4 to 1:6.

The present invention points to the advantages of a composition comprising a combination of one NRI and one SSRI, wherein in a preferred embodiment the one NRI is reboxetine and the one SSRI is fluoxetine. According to some embodiments, the amount of reboxetine is at most 6 mg and the amount of fluoxetine is at most 20 mg. According to other embodiments, the ratio of reboxetine to fluoxetine is within the range of 1:4 to 1:6, wherein according to a preferred embodiment the ratio is 1:5.

Reboxetine ((R*,R*)-2-[(2-ethoxyphenoxy)-phenylmethyl]morpholine) is a selective norepinephrine reuptake inhibitor, with only marginal serotonin and no dopamine reuptake inhibitory activity. Reboxetine displays no anticholinergic binding activity in different animal models, and is substantially devoid of monoamine oxidase (MAO) inhibitory activity. Reboxetine has been shown to be effective in the short and long term treatment of depression as well as ADHD. Chemically, reboxetine has two chiral centers and, therefore, exists as two enantiomeric pairs of diastereomers, the (R,R)-, (S, S)-, (R, S)-, and (S,R)-isomers.

Fluoxetine, (+−)-N-methyl-3-(p-trifluoromethylphenoxy)-3-phenylpropyl-amine, is a member of the SSRI class medication which acts to selectively inhibit the uptake of serotonin by the neurons in the central nervous system. Fluoxetine is indicated for the treatment of depression, obsessive-compulsive disorder, and bulimia nervosa and is commonly administered orally as a solution or in tablets in an average of about 10 mg/day to about 60 mg/day.

It has been disclosed that reboxetine and fluoxetine act as intermediate P-glycoprotein (Pgp) inhibitors (Weiss et al. J Pharmacol Exp Ther. 2003, 305(1):197-204). Pgp is responsible for the efflux of many drugs, contributing to their renal and biliary elimination. Accordingly, Pgp inhibition by drugs may increase plasma and brain concentrations of coadministered drugs and consequently may cause adverse drug reaction. Thus, the prior art apparently teaches away from the use of the combination of fluoxetine and reboxetine, due to the possible drug safety concern; however, as disclosed in the present invention, the doses of fluoxetine and reboxetine administered are very low, taken together with their intermediate inhibition properties of Pgp, the likelihood of adverse drug reaction is low.

A combination of SSRIs and NRIs, including fluoxetine and reboxetine, for treating and preventing an extensive list of disorders is disclosed in US 2005/0014848. The extensive list includes editing disorder, as well as, depression, anxiety disorders, phobias, avoidant personality disorder, chemical dependencies, Parkinson's diseases, obsessive-compulsive disorder, negative symptoms of schizophrenia, premenstrual syndrome, headache and a combination thereof in a mammal. According to the specification of US 2005/0014848, the method comprises administering to a mammal in need of such treatment or prevention an SSRI, such as, fluoxetine among other SSRIs and an NRI, such as, reboxetine, among other NRIs. Regarding the amount of the active ingredients, wide ranges are disclosed, specifically, about 6 mg to about 80 mg for fluoxetine, about 1 mg to about 30 mg for racemic-reboxetine and about 1 mg to about 20 mg for (S,S)-reboxetine. The disclosure of US 2005/0014848 does not provide any guidance as to the preferred dosages of each of the SSRI or NRI and does not even suggest preferred ratios between the active pharmaceutical ingredients.

Advantageously, the present invention discloses specifically low doses for each of the active components in the claimed combination. Furthermore, the pharmaceutical combination of the present invention is drawn to particular ratios between the amounts of the two active ingredients. In particular, the pharmaceutical composition of the present invention, in a preferred embodiment comprises reboxetine and fluoxetine, wherein the amount of reboxetine is at most 6 mg and the amount of fluoxetine is at most 20 mg and wherein the ratio between reboxetine and fluoxetine, is within the range of 1:4 to 1:6. In a preferred embodiment the ratio of reboxetine to fluoxetine is 1:5.

The present invention also provides a method for the treatment of obesity, comprising administering to a subject in need thereof a pharmaceutical composition comprising at least one NRI and at least one SSRI, wherein the amount of the at least one NRI is at most 6 mg/day and the amount of the at least one SSRI is at most 20 mg/day and wherein the ratio of the at least one NRI to at least one SSRI is within the range of 1:4 to 1:6.

Additionally, the present invention also provides a pharmaceutical composition for the treatment of obesity, wherein the pharmaceutical composition comprises at least one NRI and at least one SSRI, wherein the amount of the NRI is at most 6 mg/day and the amount of the SSRI is at most 20 mg/day and wherein the ratio of the NRI to SSRI is within the range of 1:4 to 1:6.

The pharmaceutical composition of the present invention can be formulated for administration by a variety of routes including oral, rectal, transdermal, subcutaneous, intravenous, intramuscular, intranasal, and topical, limited only by the physical properties of the active components of the composition and by the convenience of the patient and the physician. For example transdermal administration may be considered for forgetful patients. Administration by injection of a solution may be desirable for patients who are adverse to treatment.

The inert ingredients and manner of formulation of the pharmaceutical compositions are conventional, except for the presence of the active combination of the NRI and the SSRI according to the doses and ratios as described herein above, further comprising an excipient or a carrier. The active compounds are formulated as pharmaceutical compositions and administered in a variety of forms such as liquid, solid, and semisolid. The compositions can be in the form of tablets, pills, powders, lozenges, sachets, cachets, elixirs, suspensions, emulsions, solutions, syrups, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methylcellulose. The formulations may additionally include lubricating agents, such as, talc, magnesium stearate and mineral oil; wetting agents; emulsifying and suspending agents; preserving agents such as methyl- and propylhydroxybenzoates; sweetening agents; and flavoring agents.

By employing procedures known in the art, the compositions may be formulated as immediate release formulations, or as controlled or sustained release formulations allowing for extended release of the active components over a predetermined time period. Techniques for formulation and administration of drugs may be found in "Remington's Pharmaceutical Sciences," Mack Publishing Co., Easton, Pa., latest edition, which is incorporated herein by reference.

For preparing solid compositions such as tablets, the principal active ingredients are mixed with a pharmaceutical excipient to form a solid preformulation composition containing a homogeneous mixture comprising the active combination of the present invention. When referring to these preformulation compositions as homogeneous, it is meant that the active components are dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two active components can be separated by an enteric layer, which serves to resist disintegration in the stomach and permit the inner component to pass intact into the duodenum or to be delayed in release. A variety of materials can be used for such enteric layers or coatings; such materials include a number of polymeric acids and mixtures of polymeric acids with materials such as shellac, cetyl alcohol, and cellulose acetate. Acid- and gastric fluid-resistant formulations are preferred. Suitable gastric fluid-resistant coatings comprise cellulose acetate phthalate, polyvinyl acetate phthalate, hydroxypropylmethylcellulose phthalate and anionic polymers of methacrylic acid and methyl methacrylate.

As detailed herein, suitable pharmaceutical compounds for oral administration may be in the form of separate units such as, for example, capsules, cachets, pastilles or tablets, each of which contains a defined amount of NRI and SSRI according to the dosages and ratios of the present invention; as powder or granules; as solution or suspension in an aqueous or nonaqueous liquid; or as an oil-in-water or water-in-oil emulsion.

The liquid forms in which the compositions of the present invention may be incorporated, for administration orally or by injection, include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

The active compounds used for formulating the pharmaceutical composition of this invention may be formulated for parenteral administration by dissolving the compounds in a suitable solvent such as an aqueous buffer and dimethyl sulfoxide or glycerol. The parenteral route may be intramuscular, intravenous, intradermal using a sustained release carrier or subcutaneous. Pharmaceutical compositions for parenteral administration may be formulated for immediate as well as sustained release. Sustained release formulations may include certain carriers which prolong the duration of the release of the active ingredient.

Transdermal delivery devices ("patches") may be formulated and used according to the present invention. Such transdermal patches may provide continuous or discontinuous infusion of the compounds of the present invention in controlled amounts. The construction and use of transdermal patches for the delivery of pharmaceutical agents is well known in the art.

Suitable pharmaceutical compositions for topical use on the skin are preferably in the form of an ointment, cream, lotion, paste, spray, aerosol or oil. Examples of suitable vehicles include petrolatum, aquaphor, neobase, propylene glycol, glycerin and the like. Combinations of two or more of these vehicles can also be used.

The term "combined therapy" as used herein refers to a combination of two therapeutic compounds for treating a patient with a disease in need thereof.

The present invention also provides a method for treating obesity comprising administering to a subject in need thereof a combined therapy comprising at least one NRI and at least one SSRI, wherein the amount of the at least one NRI is at most 6 mg/day and the amount of the at least one SSRI is at most 20 mg/day and wherein the ratio of the at least one NRI to at least one SSRI is within the range of 1:4 to 1:6. It can likewise be administered to obese patients in any age group for which both specific active components of said combined therapy is approved for treatment.

Preferably, the NRI is reboxetine and the SSRI is fluoxetine wherein the reboxetine:fluoxetine ratio is in the range of 1:4 to 1:6. According to a preferred embodiment reboxetine and fluoxetine are provided at a ratio of 1:5. For example, for a patient suffering from obesity, according to the present invention such a patient may be treated by a combined therapy comprising 4 mg/day of reboxetine and 10 mg/day of fluoxetine to be administered once a day. Other dosages and multiple daily administrations can be considered.

According to some embodiments, the treatment is administered in a single formulation comprising both compounds. According to another embodiment, the administration is at fixed intervals, usually once to thrice daily. According other embodiments, the administration occurs at variable intervals wherein the time between administrations will vary according to the general condition of the patient, and will be decided by the therapist.

According to some embodiments, the treatment is administered in separate formulations, one formulation comprising the NRI and the other formulation comprising the SSRI. According to one embodiment, both formulations may be administered concomitantly. For example, a capsule with one formulation is ingested immediately before a capsule with the other formulation is similarly ingested. Alternatively, according to another embodiment, the formulations may be administered sequentially. For example, a capsule with one component is ingested in the morning and a capsule with the other component is ingested in the evening.

It will be understood, however, that the amount of the composition actually administered will be determined by a physician, in light of the relevant circumstances, including, the chosen route of administration, age, weight, response of the individual patient and the severity of the patient's symptoms.

The present invention will now be illustrated by the following examples which are intended to be construed in a non-limitative fashion.

EXAMPLES

Example 1

Effectiveness of a Combination of Fluoxetine and Reboxetine on Weight Loss

The study was carried out on two obese female subjects without a history of depression or eating disorder and that were not on any diet.

The first subject was a 62 years old female with hypertension, dyslipidemia, and primary biliary cirrhosis. The first subject was administered (by oral uptake, self administration), each morning, 1 mg/day of reboxetine and 5 mg/day of fluoxetine, simultaneously. Patient was instructed to continue daily activities without attempting to change eating habits or go on a diet. After 2 days treatment was found to be well tolerated and the doses were increased to 2 mg/day of reboxetine and 10 mg/day of fluoxetine. After 3 weeks of treatment the subject lost 2.4 Kg. No adverse events were observed during treatment.

The second subject was a 42 years old healthy female. Subject was administered (by oral uptake, self administration), each morning, 2 mg/day of reboxetine and 10 mg/day of fluoxetine, simultaneously. Subject was instructed to continue daily activities without attempting to change eating habits or go on a diet. This subject was treated for 8 weeks and lost during this period 7.8 Kg. This subject reported dryness of the mouth from day 1 to day 3 of the treatment, which was resolved spontaneously without changing the treatment regimen.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for treating obesity, the method comprising: administering to a subject in need thereof a pharmaceutical composition comprising at least one norepinephrine reuptake inhibitor ("NRI") and at least one selective serotonin reuptake inhibitor ("SSRI");
wherein an amount of the at least one NRI is at most 6 mg/day and an amount of the at least one SSRI is at most 20 mg/day;
wherein the NRI:SSRI ratio is within the range of 1:4 to 1:6; and
wherein the pharmaceutical composition comprises reboxetine and fluoxetine as the only active ingredients, thereby inducing weight loss.

2. The method of claim 1, wherein an amount of the reboxetine is within a range of 0.1 mg to 6 mg.

3. The method of claim 1, wherein the amount of the fluoxetine is within a range of 0.1 mg to 20 mg.

4. The method of claim 1, wherein the NRI:SSRI ratio is about 1:5.

5. The method of claim 1, wherein the pharmaceutical composition is administered by a route selected from the group consisting of oral, transdermal, percutaneous, intravenous, intramuscular, intranasal, and intrarectal.

6. The method of claim 1, wherein the obesity is selected from the group consisting of overweight, obesity with binge eating disorder, and obesity without binge eating disorder.

7. The method of claim 1, wherein the subject has mass index (BMI) of at least 30 kg/m$^2$.

* * * * *